United States Patent
Gupta

(10) Patent No.: US 8,805,499 B1
(45) Date of Patent: Aug. 12, 2014

(54) CARDIAC PACEMAKERS AND PACING METHODS

(75) Inventor: Himanshu Gupta, Birmingham, AL (US)

(73) Assignee: Himanshu Gupta, Birmingham, AL (US)

( * ) Notice: Subject to any disclaimer, the term of this patent is extended or adjusted under 35 U.S.C. 154(b) by 395 days.

(21) Appl. No.: 13/028,884

(22) Filed: Feb. 16, 2011

Related U.S. Application Data

(60) Provisional application No. 61/305,061, filed on Feb. 16, 2010.

(51) Int. Cl.
*A61N 1/00* (2006.01)

(52) U.S. Cl.
USPC ........................ 607/9; 607/4; 607/5

(58) Field of Classification Search
USPC ............. 607/9–18, 27–31, 4–7; 600/508–509
See application file for complete search history.

(56) References Cited

U.S. PATENT DOCUMENTS

| | | | |
|---|---|---|---|
| 4,928,688 A | 5/1990 | Mower | |
| 5,334,220 A * | 8/1994 | Sholder | 607/9 |
| 5,450,846 A * | 9/1995 | Goldreyer | 600/374 |
| 5,609,621 A | 3/1997 | Bonner | |
| 5,741,308 A * | 4/1998 | Sholder | 607/9 |
| 6,208,901 B1 * | 3/2001 | Hartung | 607/23 |
| 6,223,079 B1 | 4/2001 | Bakels et al. | |
| 6,266,563 B1 * | 7/2001 | KenKnight et al. | 607/5 |
| 6,275,730 B1 | 8/2001 | KenKnight et al. | |
| 6,484,057 B2 | 11/2002 | Ideker et al. | |
| 6,643,546 B2 | 11/2003 | Mathis et al. | |
| 6,749,630 B2 | 6/2004 | McCarthy et al. | |
| 2002/0193836 A1 | 12/2002 | Schmidt | |
| 2004/0106958 A1 | 6/2004 | Mathis et al. | |
| 2005/0203580 A1 | 9/2005 | Prentice et al. | |
| 2006/0142811 A1 | 6/2006 | Militello | |
| 2006/0173503 A1 * | 8/2006 | Baynham | 607/9 |
| 2006/0173504 A1 | 8/2006 | Zhu et al. | |
| 2008/0009910 A1 | 1/2008 | Kraetschmer et al. | |
| 2010/0286742 A1 * | 11/2010 | Baynham | 607/24 |

OTHER PUBLICATIONS

Byrne et al., "Diminished left ventricular dyssnchrony and impact of resynchronization in failing hearts with right versus left bundle branch block," J. American Coll. Cardiology 50(15):1484-90 (2007).
Castellanos et al., "Measurement of conduction times with catheter electrodes during pacing from different ventricular sites," British Heart Journal 37:242-8 (1975).
Dubin et al., "Electrical resynchronization: a novel therapy for the failing right ventricle," Circulation 107:2287-9 (2003).
Fantoni et al., "Right and left ventricular activation sequence in patients with heart failure and right bundle branch block," J. Cardiovasc. Electrophysiol. 16:112-9 (2005).
Gammage and Marsh, "Randomized trials for selective site pacing: do we know where we are going?," Pacing and Clin. Electropysiology 27:878-82 (2004).
Gillis, "Redefining physiologic pacing: lessons learned from recent clinical trials," Heart Rythm 3(11):1367-72 (2006).

(Continued)

*Primary Examiner* — Catherine Voorhees
(74) *Attorney, Agent, or Firm* — Meunier Carlin & Curfman LLC

(57) ABSTRACT

Cardiac pacemakers and methods of pacing a heart are disclosed.

5 Claims, 13 Drawing Sheets

(56) References Cited

OTHER PUBLICATIONS

Klein et al., "Noninvasive delineation of normal right ventricular contractile motion with magnetic resonance imaging myocardial tagging," Annals Biomed. Engineering 26:756-63 (1998).

Lewicka-Nowak et al., "Right ventricular apex versus right ventricular outflow tract pacing: prospective, randomised, long-term clinical and echocardiographic evaluation," Kardiol. Pol. 64(10):1082-91 (2006).

Lieberman et al., "Ventriculars pacing lead location alters systemic hemodynamics and left ventricular function in patients with and without reduced ejection fraction," J. American Coll. Cardiology 48:1634-41 (2006).

Occhetta et al., "Prevention of ventricular desynchronization by permanent para-hisian pacing after antrioventricular node ablation in chronic atrial fibrillation," J. American Coll. Cardiology 47(10):1938-45 (2006).

Prinzen et al., "Mapping of regional myocardial strain and work during ventricular pacing: experimental study using magnetic resonance imaging tagging," J. American Coll. Cardiology 33(6):1735-1742 (1999).

Sweeney et al., "Adverse effect of ventricular pacing on heart failure and atrial fibrillation among patients with normal baseline QRS duration in a clinical trial of pacemaker therapy for sinus node dysfunction," Circulation 107:2932-7 (2003).

Thambo et al., "Detrimental ventricular remodeling in patients with congenital complete heart block andchronic right ventricular apical pacing," Circulation 110:3766-72 (2004).

Tops et al., "Right ventricular pacing can induce ventricular dyssynchrony in patients with atrial fibrillation after atrioventricular node ablation," J. American Coll. Cardiology 48:1642-8 (2006).

Tse et al., "Functional abnormalities in patients with permanent right ventricular pacing," J. American Coll. Cardiology 40(8):1451-8 (2002).

Tse and Lau, "Selection of permanent ventricular pacing site: how far should we go?," J. Americano Coll. Cardiology 48:1649-51 (2006).

Victor et al., "Optimal right ventricular pacing site in chronically implanted patients," J. American Coll. Cardiology 33 (2):311-316 (1999).

Victor and Ravindran, "Anatomical factors influencing fixation of endocardial pacing leads in the right ventricle," Texas Heart Institute Journal 12(1):23-32 (1985).

Vignon et al., "Quantitative assessment of regional right ventricular function with color kinesis," Am. J. Respir. Crit. Care Med. 159:1949-59 (1999).

Vlay, "Right ventricular outflow tract pacing: practical and beneficial. A 9-year experience of 460 consecutive implants," Pacing Clin. Electrophysiol. 29(10):1055-62 (2006).

Wilikoff et al., "Dual-chamber pacing or ventricular backup pacing in patients with an implantable defibrillator: the dual chamber and VVI implantable defibrillator," J. American Med. Assoc. 288:3115-23 (2002).

Wrobleski et al., "Multi-site ventricular pacing increases cardiac output compared with right ventricular apical pacing in dogs with hear failure," J. American Coll. Cardiology, Abstract 897-1 (1998).

\* cited by examiner

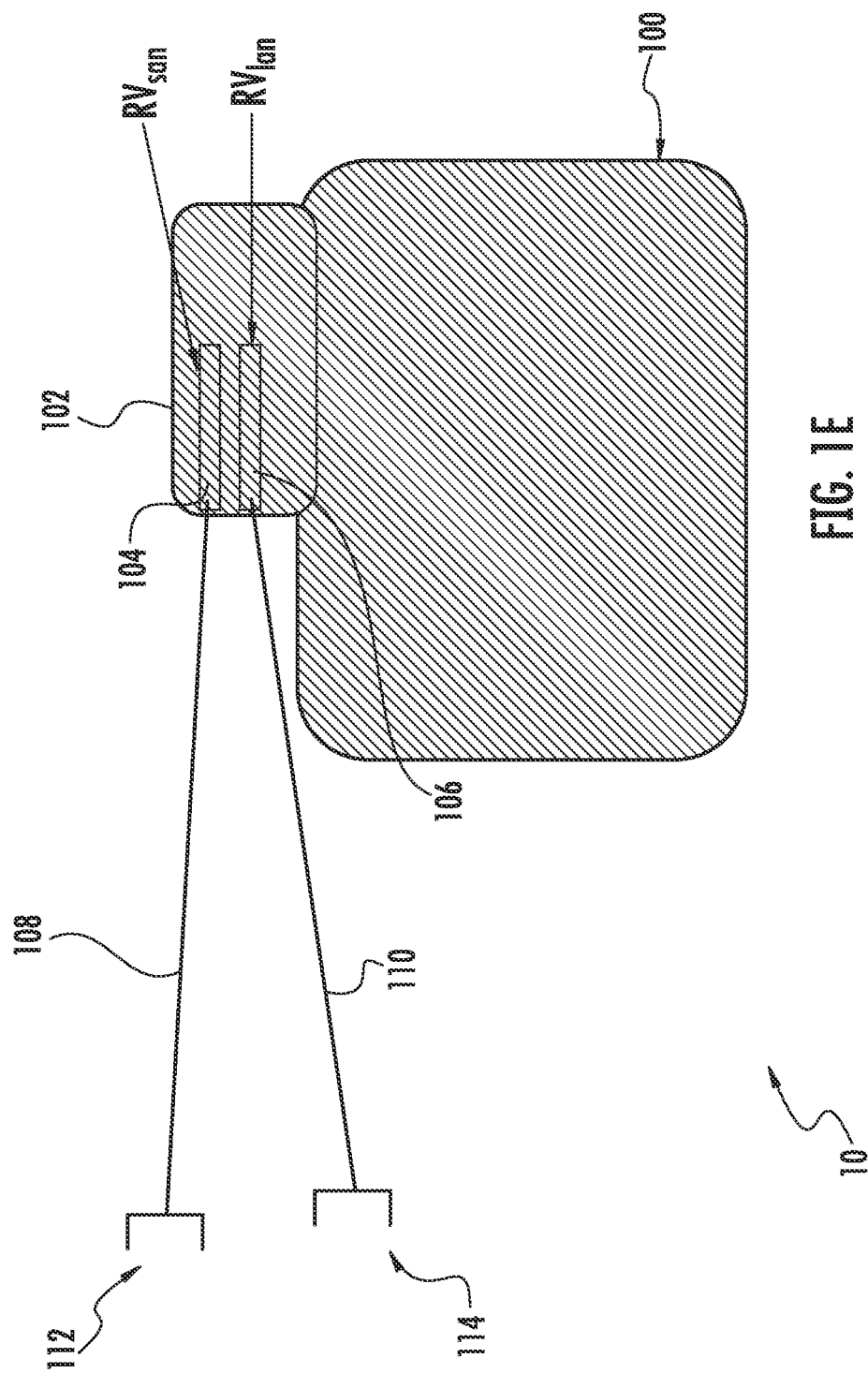

CARDIAC PACEMAKERS AND PACING METHODS

CROSS REFERENCE TO RELATED APPLICATIONS

This application claims the benefit of U.S. Provisional Application No. 61/305,061, filed on Feb. 16, 2010, which is incorporated by reference herein in its entirety.

FIELD OF THE INVENTION

The present disclosure relates to cardiac pacemaker devices, systems and methods.

BACKGROUND

Cardiac pacemakers are used to treat or manage cardiac abnormalities and pathology. Pacemaker leads are positioned in the heart to deliver electrical pulses to the myocardium. The standard location for pacing the right ventricle with a pacemaker is at the right ventricular apex.

SUMMARY

Cardiac pacemakers and methods of pacing a heart are disclosed. For example, provided is a cardiac pacemaker that comprises a pulse generator adapted to produce one or more electrical pulses for transmission to a heart. The cardiac pacemaker can further comprise at least a first electrode in communication with the pulse generator. The first electrode is adapted to be operatively positioned to transmit an electrical stimulation pulse selectively to the tricuspid annular region of the heart. The cardiac pacemaker can further comprise a control unit in communication with the pulse generator. The control unit is configured to trigger a stimulation pulse from the pulse generator for transmission to the tricuspid annular region of the heart.

An example method of pacing a heart comprises positioning an electrode relative to the heart so that an electrical stimulation pulse can be transmitted selectively to the tricuspid annular region of the heart. The method can further comprise transmitting an electrical stimulation pulse through the electrode selectively to the tricuspid annular region of the heart. The electrical stimulation pulse can cause electrical activity in the heart and can provide pacing of the heart.

The details of aspects of the devices, systems and methods are set forth in the accompanying drawings and the description below. Other features, objects, and advantages will be apparent from the description and drawings, and from the claims.

DESCRIPTION OF DRAWINGS

FIG. 1E is a schematic diagram illustrating an example cardiac pacemaker.

DETAILED DESCRIPTION

Figure 1A:
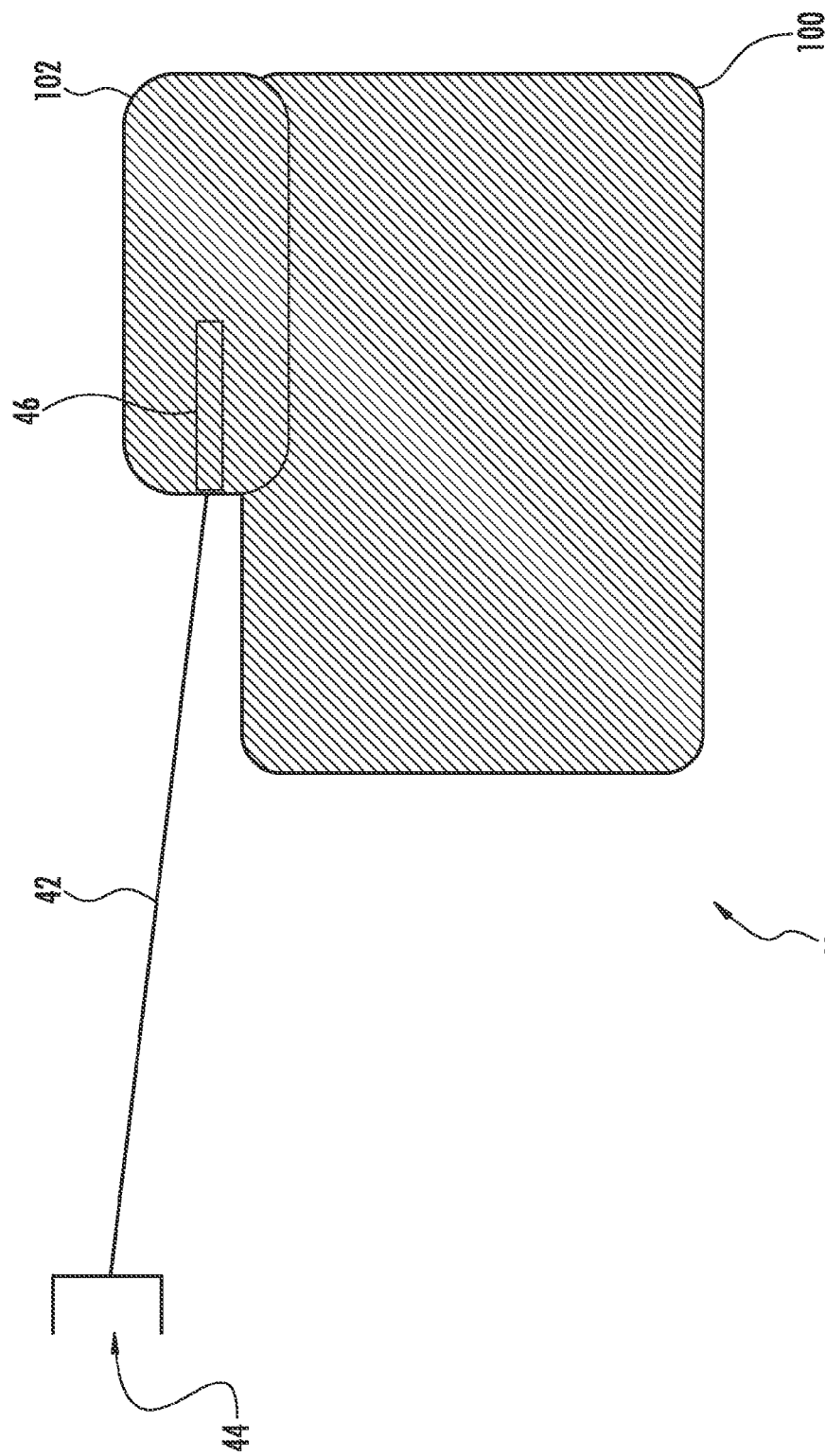
FIG. 1A is a schematic diagram illustrating an example cardiac pacemaker.

The following detailed description should be read with reference to the drawings in which similar elements in different drawings are numbered the same. The drawings, which are not necessarily to scale, depict illustrative embodiments and are not intended to limit the scope of what is claimed.

The heart has two major pumping chambers: 1) the right ventricle (RV) and 2) the left ventricle (LV). There are significant differences in the mechanical properties of RV and LV. The RV is predominantly a volume pump that pumps blood against low resistance pulmonary vasculature. In contrast, the LV pumps against high resistance systemic arterial circulation. The RV has a complex shape and can be divided into three major parts: RV inflow (that includes the tricuspid annulus), RV body and RV outflow. RV tricuspid annular motion and RV body contraction are the major contributors to the RV function. RV outflow (also known as the infundibulum) is predominantly a conduit region that has minimal contribution to RV function.

Dysfunction of either heart chamber (RV, LV) due to any underlying pathology can lead to the condition known as heart failure. Heart failure is one of the major causes of mortality and morbidity in populations throughout the world. The economic burden of heart failure is significant. Multiple therapeutic approaches have been developed for heart failure. Still, however, the incidence and prevalence of heart failure continues to rise.

Recently, cardiac resynchronization therapy has been a major focus of clinical development in the treatment of heart failure. In this approach, electrodes are implanted in the RV and the LV that are connected to a pacemaker to improve the contractile pattern of the LV leading to improved LV function. This is associated with improvement in symptoms and reduction in mortality in a select subset of patients with heart failure. However, this approach has largely ignored the important contribution of the RV to overall cardiac function. RV failure either secondary to LV dysfunction, or due to primary RV involvement, is associated with poor clinical prognosis.

The described cardiac pacemakers and methods can activate the tricuspid annulus by selectively transmitting one or more electrical pulses to the tricuspid annulus. Selective transmission of one or more electrical pulses to given target tissue (e.g. tricuspid annulus) means that that at least one pulse of electricity is transmitted from a source (e.g. an electrode of a pacing lead) that is in electrical communication with the target tissue directly to the desired target tissue (e.g. the tricuspid annulus, or portions thereof). The term does not imply that electricity selectively transmitted directly to a target tissue necessarily remains within the target tissue. The described pacemakers and methods can improve the function of the right ventricle. The devices and methods can also be used to avoid or diminish the adverse consequences of conventional RV pacing on cardiac function. Further, the devices and methods can be used to improve tricuspid annular motion, RV systolic and diastolic function, RV and LV energetics, RV-LV synchronicity, LV systolic and diastolic function, interventricular septal interaction, myocardial perfusion, and atrial-ventricular interaction. The devices and methods can also narrow the time taken to electrically activate the ventricles in the presence of right bundle branch block (RBBB), decrease tricuspid regurgitation, and can prevent atrial fibrillation and other arrhythmia.

FIG. 1A is a schematic diagram of an example cardiac pacemaker device 40 for transmission of an electrical pulse selectively to the tricuspid annular region of a subject heart. The tricuspid annular region includes the septal annular region of the tricuspid annulus and/or the lateral annular region of the triscuspid annulus.

The cardiac pacemaker device 40 can include a pulse generator 100 and a header portion 102. The header portion 102 can have at least one lead receptacle 46. The pacemaker 40 can be electrically coupled to a heart at the tricuspid annular region by connecting one or more leads 42 to the lead receptacle 46, and electrically coupling one or more leads 42 to tissue of the heart in a location to selectively deliver one or more electrical pulses to the tricuspid annular region. A lead 42 can be electrically coupled to the heart tissue using one or more electrodes 44. A lead 42 can be electrically coupled to the pulse generator 100 by connecting the lead 42 to the lead receptacle 46.

An electrode 44 in communication with the at least one lead 42 can be positioned relative to the heart such that one or more electrical stimulations (e.g. electrical pulses) can be selectively delivered to the tricuspid annular region of the heart. The lead 42 can be unipolar or bipolar. A unipolar lead can be configured to stimulate the tricuspid annular region of the heart. A bipolar lead can be configured to stimulate the tricuspid annular region and can also sense electrical activity selectively from the tricuspid annular region.

Figure 1B:
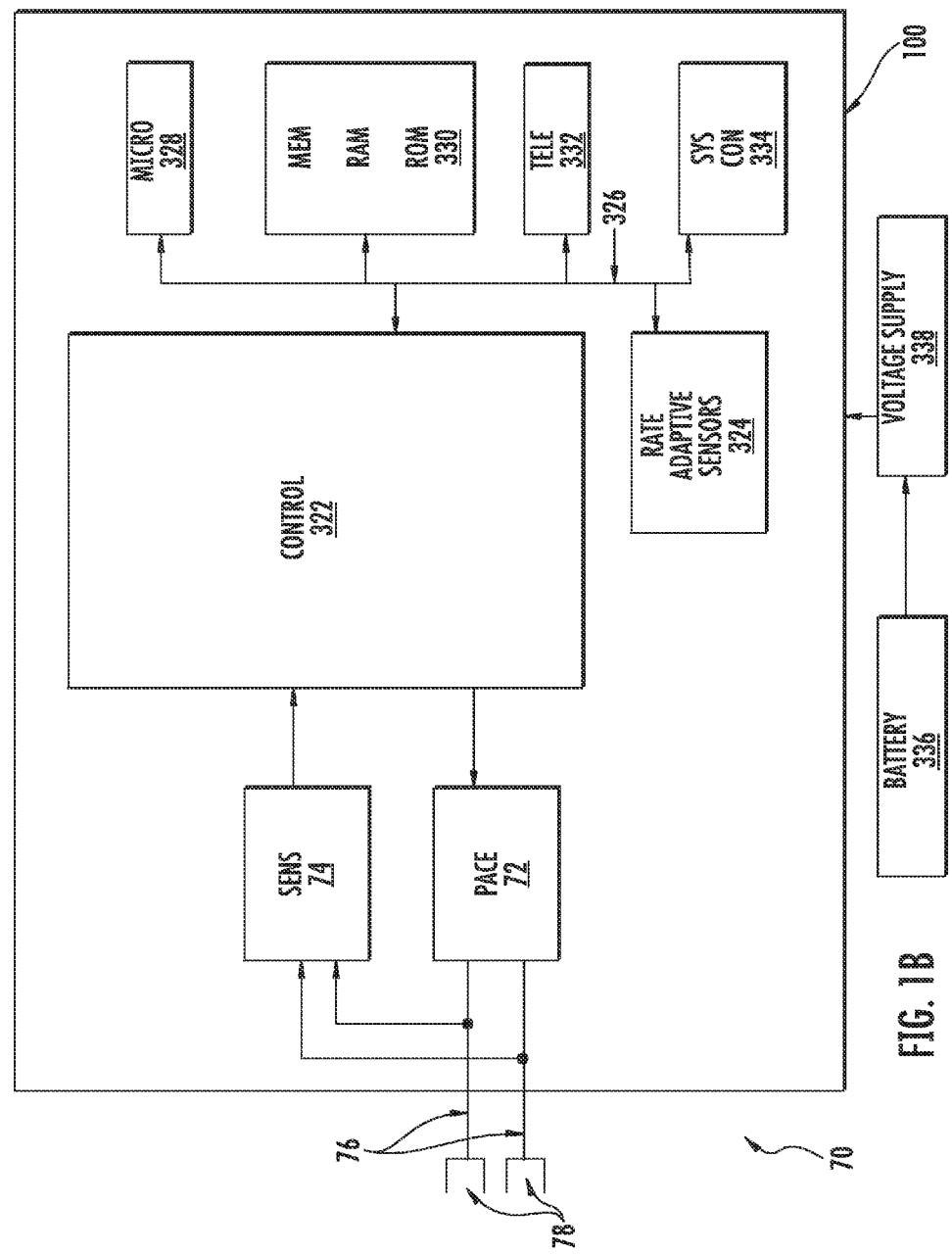
FIG. 1B is a block diagram showing aspects of an example cardiac pacemaker.

FIG. 1B is a block diagram illustrating aspects of an example cardiac pacemaker, such as the pacemaker 40 shown schematically in FIG. 1A. The example cardiac pacemaker can include a bipolar lead 76 in communication with electrodes 78 for sensing electrical activity in the heart and for delivering one or more electrical pulses for pacing the heart. As described above, the lead can also be a unipolar lead comprising an electrode for delivering one or more electrical pulses for pacing the heart.

Optionally, the electrodes 78 can be positioned in the heart relative to the tricuspid annular region of the heart such that they can selectively sense electrical activity from the tricuspid annular region of the heart and so that they can deliver one or more electrical pulses to the tricuspid annular region of the heart.

For example, the electrodes 78 can be positioned relative to the heart so that they can selectively detect electrical activity from the septal annular region of the tricuspid annulus or so that they can be used to selectively deliver one or more electrical pulses to the septal annular region of the tricuspid annulus to provide pacing to the tricuspid annular region.

Electrical activity sensed by the electrodes 78 can be communicated to the sensing unit 74, and one or more electrical pulses can be generated using a pacing unit 72 of the pulse generator 100 for delivery to the heart. Thus, the pulse generator 100 can comprise a pacing unit 72 that includes circuitry for providing the electrical output stimulus. The pacing unit 72 is in electrical communication with the lead 76. Thus, the pacing unit 72 comprises circuitry configured to provide an electrical stimulus having predetermined electrical characteristics for selective delivery to the tricuspid annular region.

The control unit 322 receives signals from the sensing unit 74 and generates trigger signals for the pacing unit 72. The trigger signals cause the pulse generator 100 to deliver an electrical pulse through the lead 76 and electrode 78 to the heart. The pacemaker 40 can further comprise memory 330 and a processor 328. The memory 330 and processor 328 can be coupled to the control unit 322 using the system bus 326. The memory 330 and processor 328 can function to direct the sensing and stimulation capabilities of the pacemaker through the control unit 322.

Optionally, the pacemaker 40 can further comprise a telemetry circuit 332 for communicating with processing systems remote to the pacemaker. The pacemaker 40 can also include a system control module 334 that can support circuitry for the processor 328, a telemetry interface 332, and a sleep-wake control.

Optionally, the pacemaker 40 can include a rate adaptive sensor 324 that is in communication with the control unit 322 through the system bus 326. The rate adaptive sensor 324 can be any sensor capable of sensing a physiological parameter related to the rate at which a heart should be beating. For example, the rate adaptive sensor can sense parameters such as oxygen content of blood, body motion, respiration rate and/or pH of blood. Parameters sensed by the rate adaptive sensor can be used to adjust aspects of the pacing timing and characteristics.

The pacemaker 40 can also comprise a battery 336, such as a lithium iodine battery, and a voltage supply 338 that can supply various current and voltage to the pulse generator 100. Optionally, the battery 336 can be integral with the pulse generator 100 or the supplied voltage can be communicated to the pulse generator 100. The pacing unit 72 can use the supplied voltage to produce an electrical stimulus for pacing the heart.

Figure 1C:
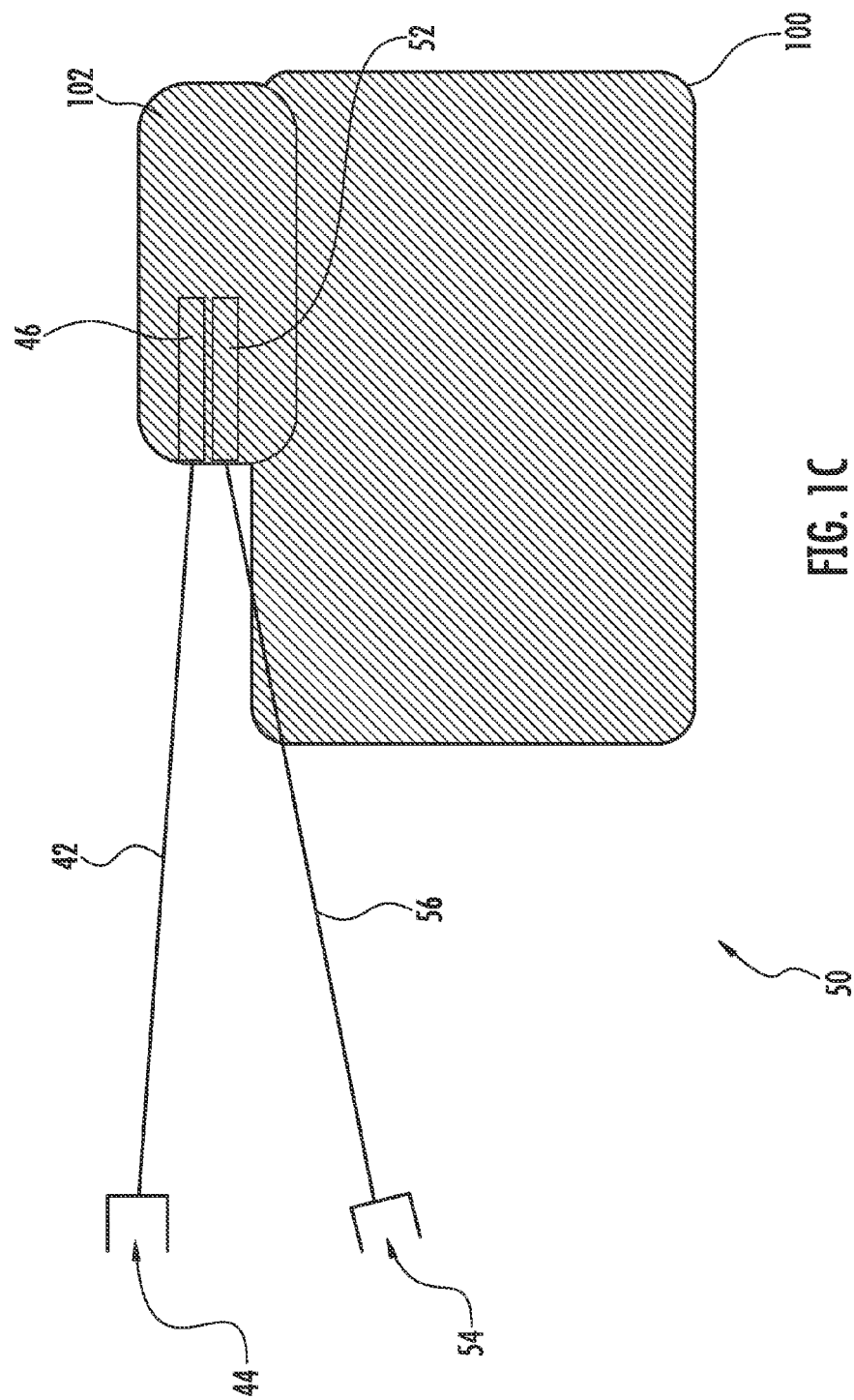
FIG. 1C is a schematic diagram illustrating an example cardiac pacemaker.

FIG. 1C is a schematic diagram of an example cardiac pacemaker device 50 for transmission of an electrical pulse selectively to the tricuspid annular region of a subject heart and for sensing and/or pacing of the right atrium. In this example, a lead 42 configured to selectively stimulate and/or detect electrical activity selectively at or from the tricuspid annular region can be used in conjunction with a lead 56 configured to sense and/or pace the right atrium. In this example, the device is a dual chamber pacemaker. The atrial lead 56 placed in the right atrium can sense electrical activity from the atrium and/or can pace the right atrium. The atrial lead 56 can be a unipolar or a bipolar lead. The right atrial lead 56 can be positioned using methods and locations used for known pacemaker applications. In addition to right atrial lead 56, the device further comprises a right ventricular lead 42, placed to selectively stimulate pacing of the right ventricle at the tricuspid annular region.

The cardiac pacemaker device 50 can include a pulse generator 100 and a header portion 102. The header portion 102 can have two lead receptacles (46 and 52). The pacemaker 50 can be electrically coupled to a heart by connecting one or more leads (42 and 56) to the lead receptacles and electrically coupling one or more lead to tissue of the heart. A lead (56 and 42) can be electrically coupled to the heart tissue using one or more electrodes (44 and 54). A lead (56 and 42) can be electrically coupled to the pulse generator 100 by connecting each lead (56 and 42) to a lead receptacle (46 and 52).

Figure 1D:
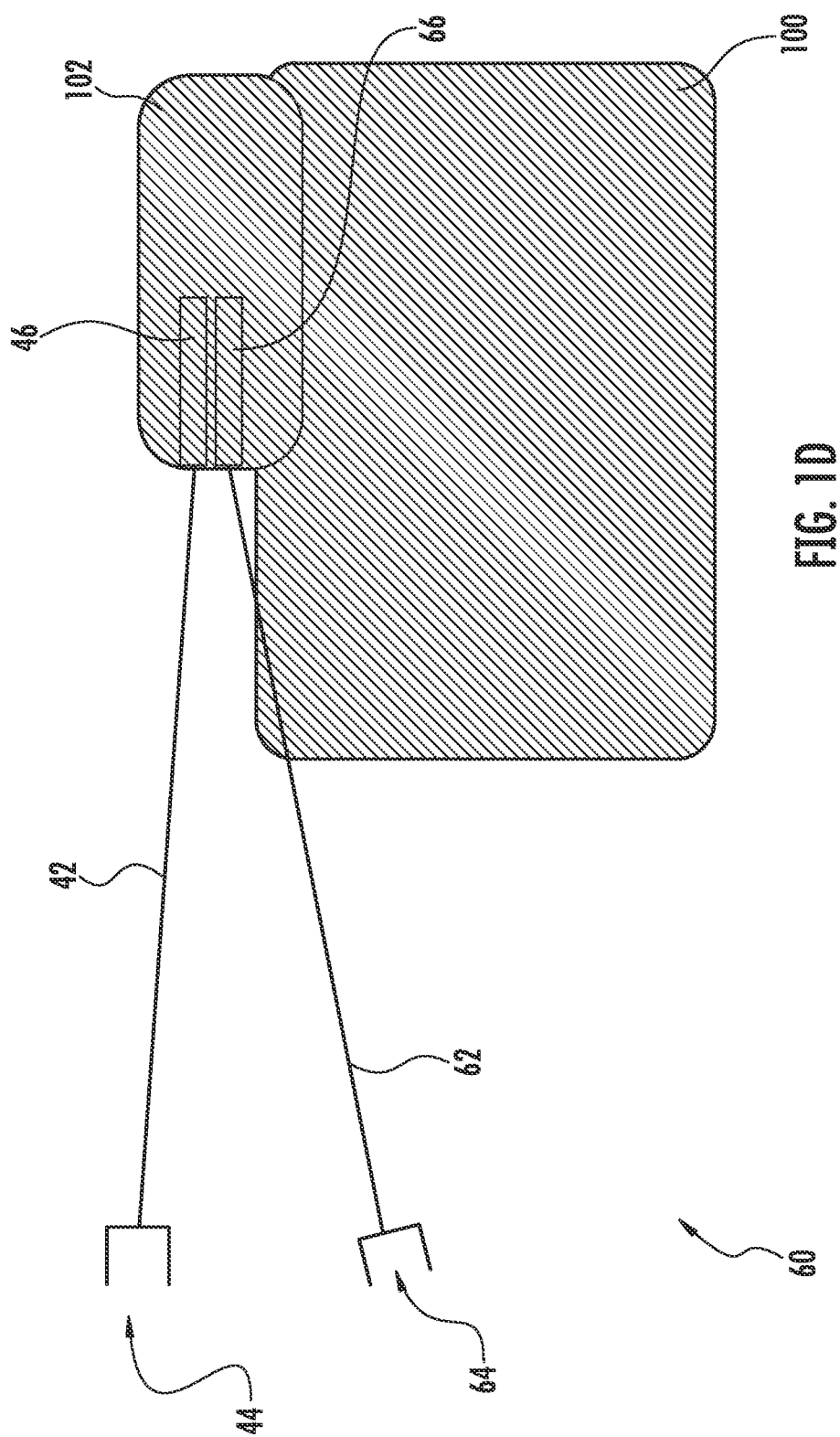
FIG. 1D is a schematic diagram illustrating an example cardiac pacemaker.

FIG. 1D is a schematic diagram of an example cardiac pacemaker device 60, having a lead 42 configured to selectively stimulate and/or detect electrical activity at the tricuspid annular region. The example device can further comprise a lead 62 for sensing and/or pacing from or at the left ventricle. The left ventricular lead 62 can be a unipolar or a bipolar lead. The left ventricular lead 62 can be positioned as known for current pacemaker applications. In this example, the device is a biventricular pacemaker. The biventricular pacemaker can be used in cardiac resynchronization therapy. For example, the timing of a right ventricular stimulus can be the same as that of a left ventricular pacing stimulus or up to 50 ms earlier or later than the left ventricular pacing stimulus. Based on the underlying cardiac pathology, the pacemaker for imparting one or more pacemaker pulses to the LV and to the tricuspid annulus can be independently programmed to generate improvement in cardiac function. For example, in right bundle branch block (RBBB) morphology, the annulus lead can pace substantially simultaneously with the LV lead to improve cardiac function. Pacing parameters can be evaluated using a pacing system analyzer (PSA). For example, pacing parameters can include R>5 mV; Threshold <2V at 1 msec. Lead placement can also be modified based on narrowing of the QRS complex or absence of widening of the QRS complex with pacing or the shortest paced QRS complex, improvement in RV and LV function measured by echocardiography as compared to baseline, and/or improvement in cardiac output or RV stroke volume. The cardiac pacemaker device 60 can include a pulse generator 100 and a header portion 102. The header portion 102 can have two lead receptacles (46 and 66). The pacemaker 60 can be electrically coupled to a heart by connecting one or more leads (42 and 62) to the lead receptacles (46 and 66) and electrically coupling one or more leads (42 and 62) to tissue of the heart. A lead (42 and 64) can be electrically coupled to the heart tissue using one or more electrodes (44 and 64). A lead (42 and 66) can be electrically coupled to the pulse generator 100 by connecting each lead (42 and 62) to a lead receptacle (46 and 66).

FIG. 1E is a schematic diagram of an example cardiac pacemaker device 10 for stimulating and/or sensing electrical activity selectively at the tricuspid annulus region. The cardiac pacemaker device 10 can include a pulse generator 100 and a header portion 102. The header portion 102 can have two lead receptacles (104 and 106). The pacemaker 10 can be electrically coupled to a heart by connecting one or more leads (108 and 110) to the lead receptacles and electrically coupling one or more lead to tissue of the heart. A lead can be electrically coupled to the heart tissue using one or more electrodes. A lead can be electrically coupled to the pulse generator 100 by connecting each lead (108 and 110) to a lead receptacle (104 and 106).

For example, a first right ventricular lead (108 or 110) can be coupled to the pacemaker device 10. A first electrode (112 or 114) in communication with the first lead can be positioned relative to the heart such that one or more electrical stimulations (e.g. electrical pulses) can be selectively delivered to the tricuspid annular region of the heart.

Optionally, the first electrode can be positioned relative to the heart such that it can deliver one or more electrical stimulations to the heart selectively at the septal annular region of the heart's tricuspid annulus. The electrode 114 can be positioned to deliver one or more electrical stimulation pulse from the lead 110 (RVsan) selectively at the septal annular region of the tricuspid annulus.

The pacemaker can also be coupled to a second lead. The second lead can be in communication with a second electrode that is positioned relative to the heart such that it can deliver one or more electrical stimulations (e.g. electrical pulses) selectively to the heart at the tricuspid annular region of the heart. Optionally, the second electrode can be positioned relative to the heart such that it can deliver one or more electrical pulses to the heart selectively at the lateral annular region of the heart's tricuspid annular region. The electrode 112 can be positioned to deliver one or more electrical stimulation pulse from the lead 108 (RVlan) selectively at the lateral annular region of the tricuspid annulus.

Electrical pulses delivered by either or both of the electrodes (112 and 114) can be used to pace the right ventricle of the heart. The leads (108 and 110) can also be configured to detect electrical activity in the tricuspid annular region of the heart. For example, the leads (108 and 110) can be bipolar and can each comprise two electrodes, one for stimulation and the other adapted to receive electrical signals for transmission to the pulse generator. If an electrode is placed in the septal annular region, then that electrode, or a second electrode of a bipolar lead, can be used detect electrical activity in the septal annular region. If an electrode is placed in the lateral annular region, then that electrode, or a second electrode of a bipolar lead, can be used to detect activity in the lateral annular region.

The pacemaker for selectively stimulating the tricuspid annular region can be a dual chamber pacemaker modified into a single chamber pacemaker. For example, the device 10 can be modified by replacing a usual atrial lead of a dual chamber pacemaker with one of the two leads (108 or 110). In this case, the other lead (108 or 110) can be placed in the second lead receptacle of the dual chamber pacemaker. The two right ventricular (RV) leads can be programmed individually based on, for example, desired stimulation characteristics and sensing characteristics. Desired stimulation and sensing characteristics can be established using a pacing system analyzer (PSA). For example, pacing parameters can include R>5 mV; Threshold <2V at 1 msec. Lead placement can also be modified based on narrowing of the QRS complex or absence of widening of the QRS complex with pacing or the shortest paced QRS complex, improvement in RV and LV function measured by echocardiography as compared to baseline, and/or improvement in cardiac output or RV stroke volume.

Figure 2:
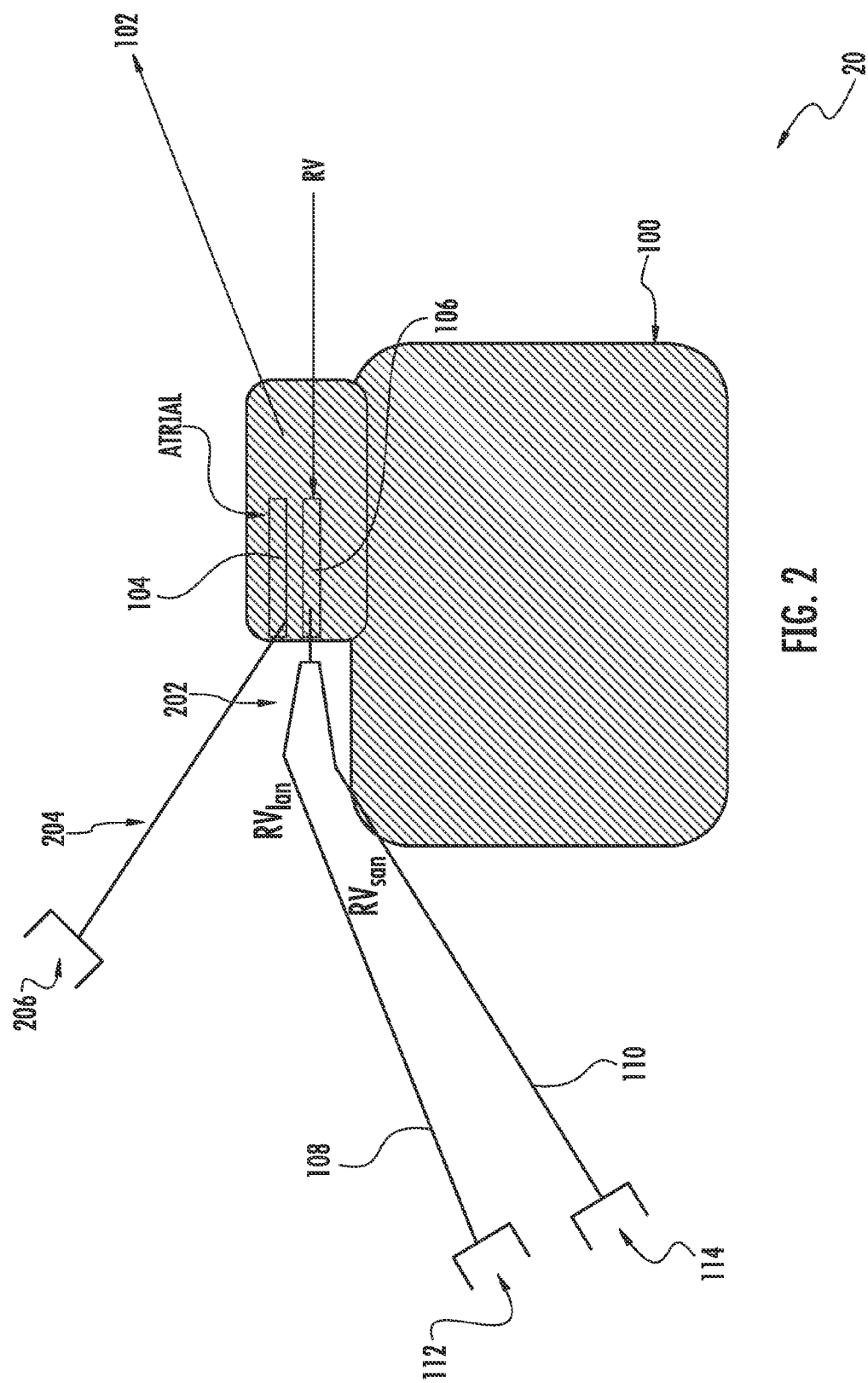
FIG. 2 is a schematic diagram illustrating an example cardiac pacemaker.

Referring to FIG. 2, an example pacemaker device 20 can be used to pace the right ventricle from the tricuspid annular region using first and second electrodes (114 and 112) positioned respectively at the lateral annular and septal annular region. The pacemaker device 20 can also include conventional atrial sense and pace capabilities.

The example pacemaker device 20 can include a header 102 having two lead receptacles (104 and 106). For the conventional atrial sense and pace capabilities, a lead 204 can be connected to the lead receptacle 104 and one or more electrode 206 in communication with the lead 204 can be positioned in electrical communication with the right atrium of the heart.

Optionally, a lead adaptor 202 can be connected to the lead receptacle 106. The lead adaptor 202 can be electrically connected to two leads (108 and 110) for pacing the heart in the tricuspid annular region. Thus, for example, a lead that can deliver an electrical pulse to the lateral annular region 110 and a lead that can deliver an electrical pulse to the septal annular region 108 can be connected with the lead adaptor 202 such that electrical pulses can be delivered through both leads by way of connection of the lead adaptor 202 to a single lead receptacle 106.

Figure 3B:
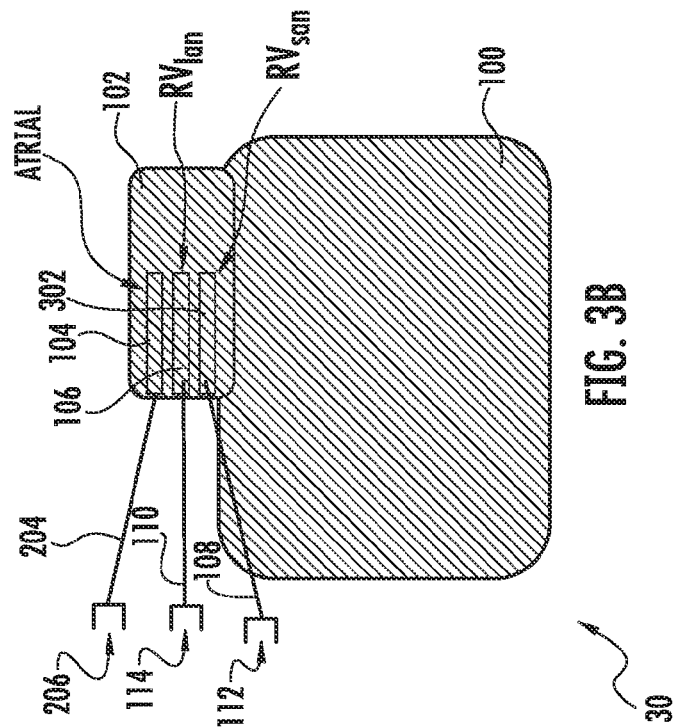
FIG. 3B is a schematic diagram illustrating an example cardiac pacemaker.
Figure 3A:
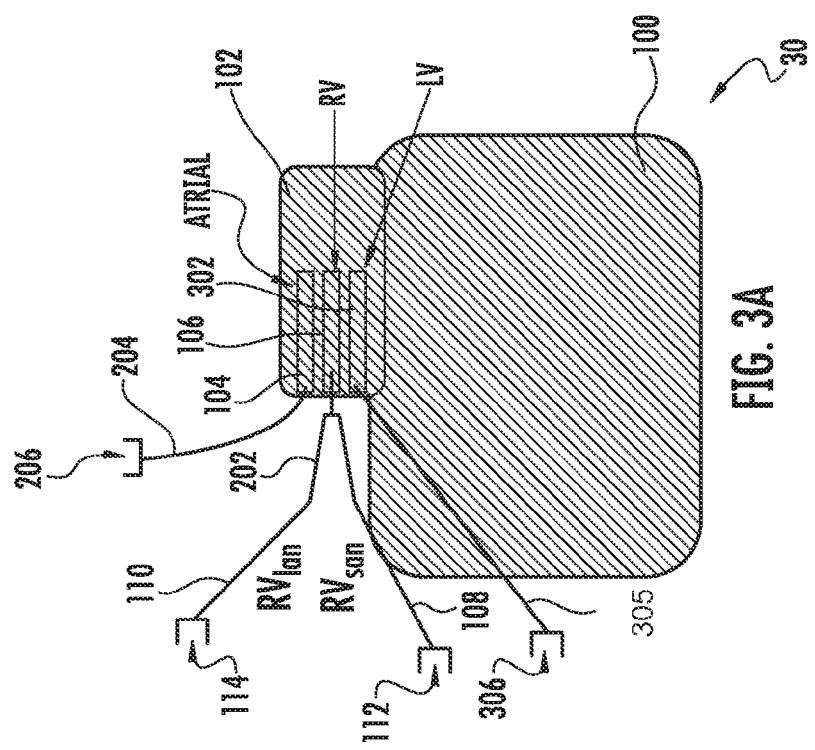
FIG. 3A is a schematic diagram illustrating an example cardiac pacemaker.

As shown in FIGS. 3A and 3B, an example pacemaker 30 can further include a third lead receptacle 302 in addition to lead receptacles 104 and 106. In FIG. 3A, one of the three receptacles, for example receptacle 104, can be connected to a lead 204 for sensing and pacing the right atrium. A second of the three receptacles, for example receptacle 106, can be connected to a lead adaptor 202. The lead adaptor 202 can be connected to two leads (108 and 110) for pacing the heart in the tricuspid annular region. For example, one lead connected to the lead adaptor 202 can be in communication with an electrode 114 positioned to selectively deliver one or more electrical pulses to the lateral annular region of the tricuspid annulus, and a second lead can be in communication with an electrode 112 positioned to selectively deliver one or more electrical pulses to the septal annular region of the tricuspid annulus.

A third of the three receptacles, for example, receptacle 302, can be connected to a lead 305 for sensing and/or pacing in the left ventricle of the heart. In this configuration, the example pacemaker has biventricular pacing capabilities.

In FIG. 3B, instead of using a left ventricular lead, two leads for selectively pacing the tricuspid annular region (110 and 108) are separated into their own lead receptacles (106 and 302) and the atrial lead is maintained in its own receptacle 104. The configuration shown in FIG. 3B thus maintains is dual chamber capabilities and each lead for pacing the tricuspid annular region can be individually programmed.

Figure 4:
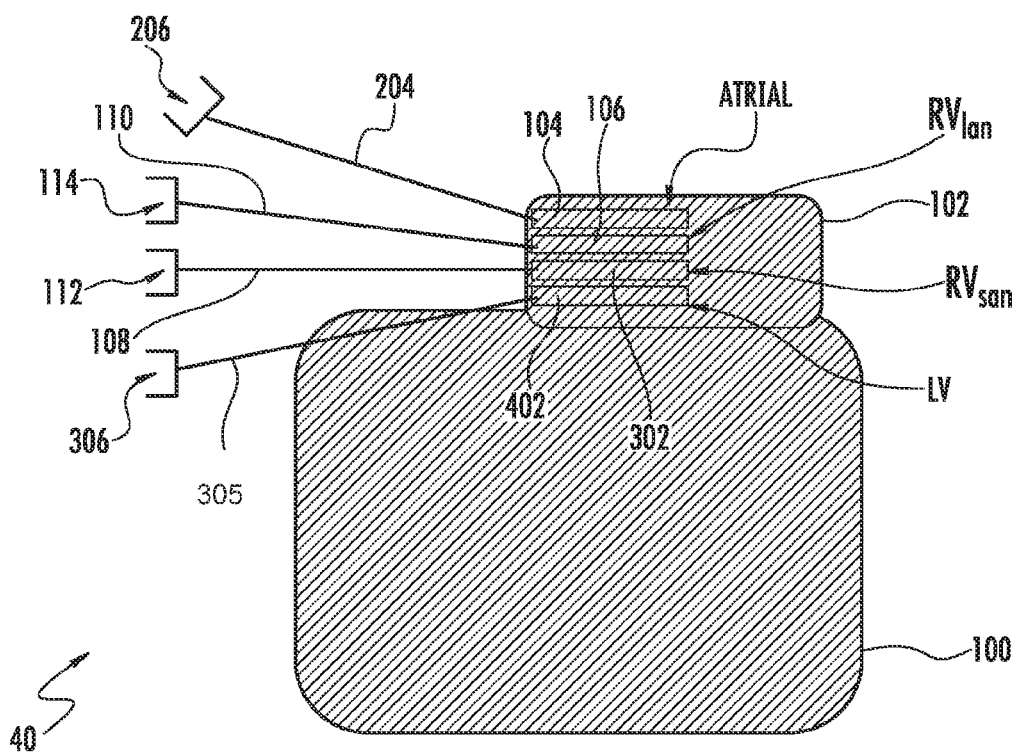
FIG. 4 is a schematic diagram illustrating an example cardiac pacemaker.

As shown in FIG. 4, another example pacemaker 40 can comprise a fourth lead receptacle 402. In this example, each lead, including a atrial lead 204, a lateral annular lead 110, a septal annular lead 108, and a left ventricular lead 305 can all be individually used to sense and stimulate a desired location of the heart. Thus, the device 40 represents an example biventricular pacemaker where the right ventricle can be paced by selectively stimulating the lateral annular region of the tricuspid annulus and/or by selectively stimulating the septal annular region of the tricuspid annulus.

Figure 3C:
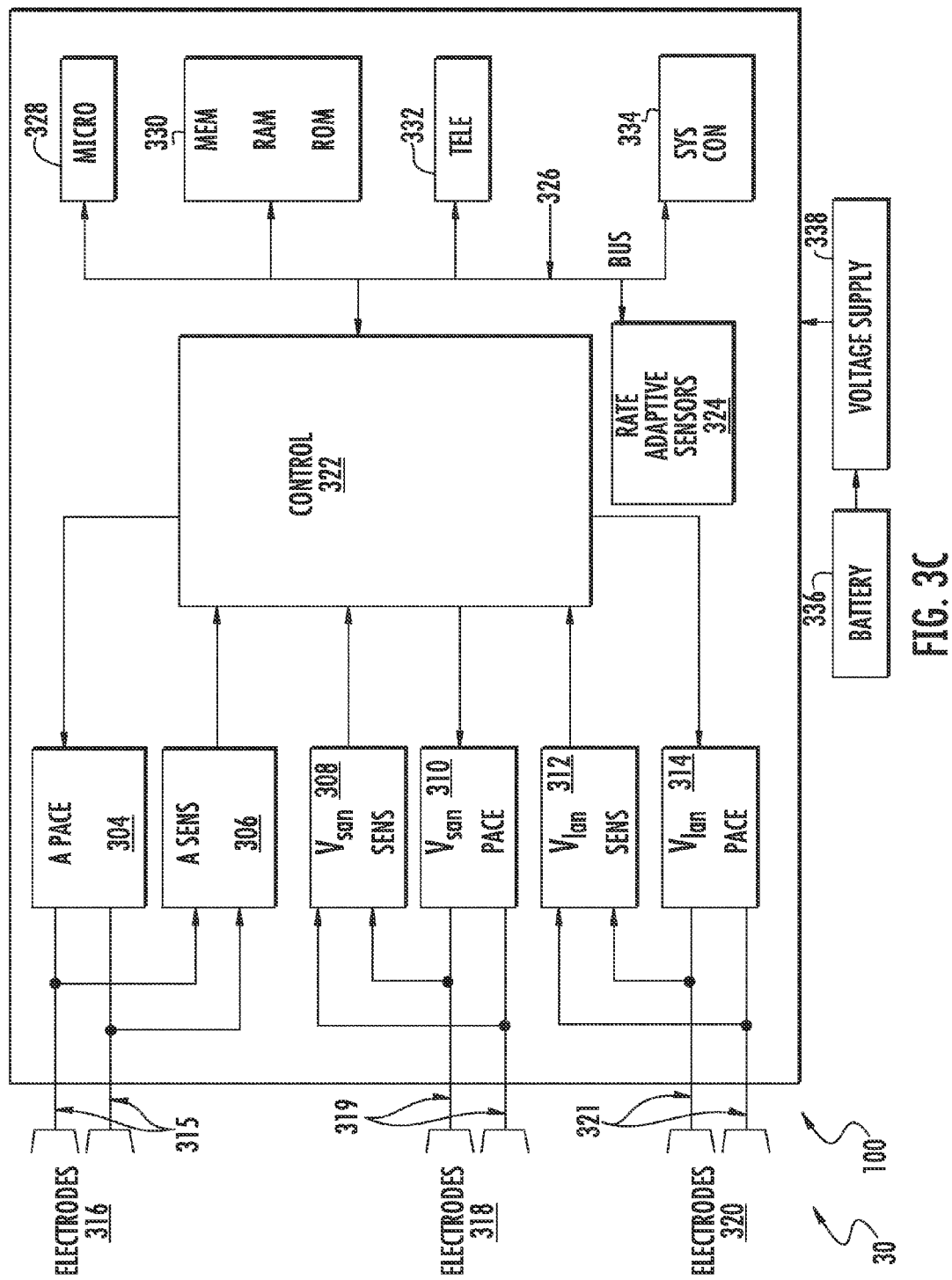
FIG. 3C is a block diagram showing aspects of an example cardiac pacemaker.
Figure 3D:
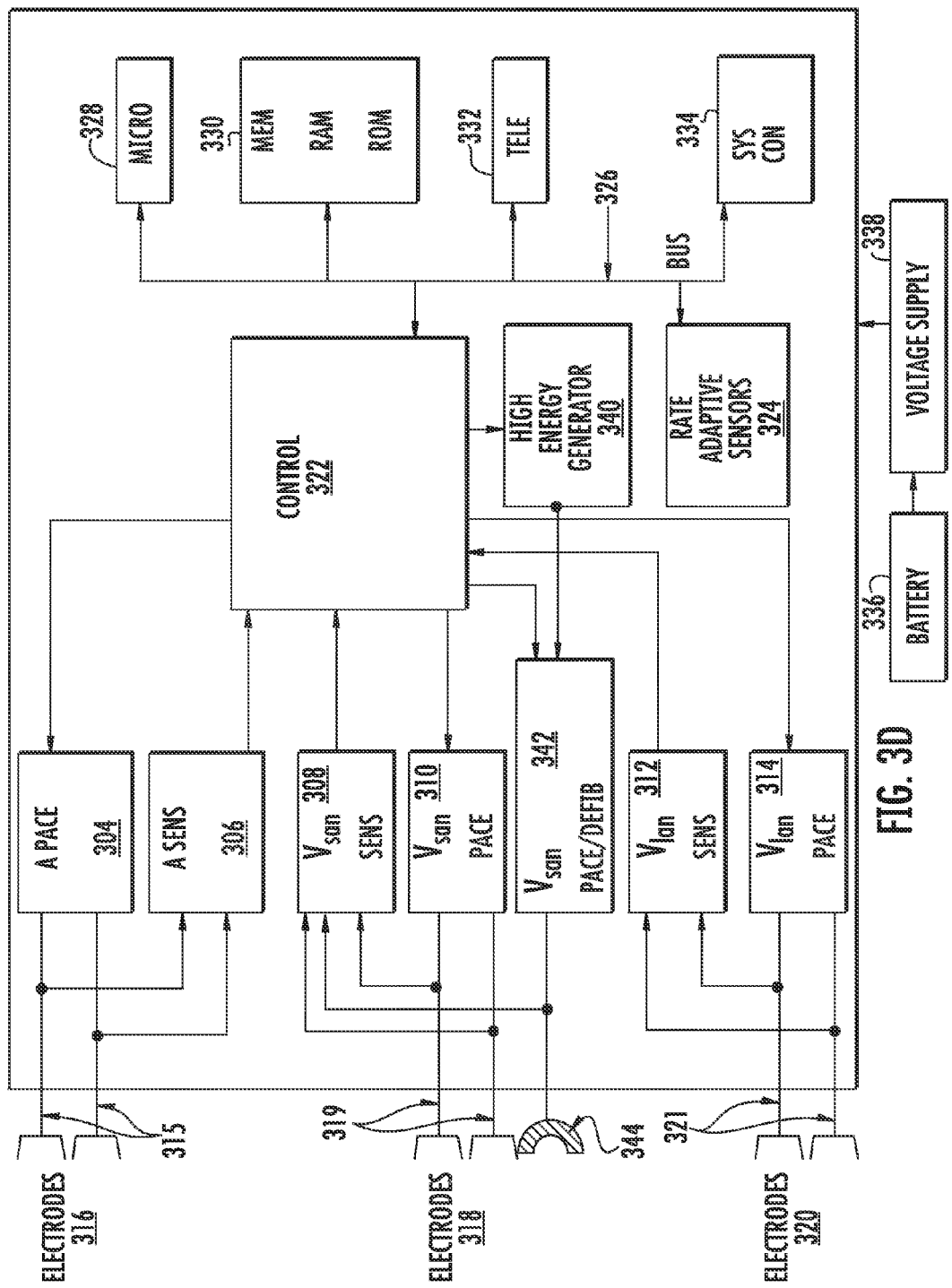
FIG. 3D is a block diagram showing aspects of an example cardiac pacemaker.

FIGS. 3C and 3D are block diagrams illustrating aspects of an example cardiac pacemaker, such as the pacemaker 30 shown schematically in FIG. 3B. The example cardiac pacemaker can include bipolar leads (315, 319 and 321) in communication with electrodes (316, 318 and 320) for sensing electrical activity in the heart and for delivering one or more electrical pulses for pacing the heart.

The electrodes 316 can be positioned in the heart in communication with the right atrium. One or more of the electrodes 316 can sense electrical activity in the right atrium and can communicate the sensed electrical activity to an atrial sensing unit 306. The sensing unit 306 can comprise circuitry for filtering, converting, and amplifying electrical signals received from the heart. One or more of the electrodes 316 can also deliver one or more electrical pulses generated by the pulse generator 100. The pulse generator can comprise an atrial pacing unit 304 that includes circuitry for providing the electrical output stimulus. The atrial pacing unit 304 is in electrical communication with the atrial lead 315. Thus, the atrial pacing unit comprises circuitry configured to provide an electrical stimulus having predetermined electrical characteristics for delivery to the atrium.

The electrodes 318 can be positioned in the heart relative to the tricuspid annular region of the heart such that they can selectively sense electrical activity from the tricuspid annular region of the heart and so that they can deliver one or more electrical pulses to the tricuspid annular region of the heart. For example, the electrodes 318 can be positioned relative to the heart so that they can selectively detect electrical activity from the septal annular region of the tricuspid annulus or so that they can be used to selectively deliver one or more electrical pulses to the septal annular region of the tricuspid annulus to provide pacing to the tricuspid annular region. Electrical activity sensed by the electrodes 318 can be communicated to the sensing unit 308, and one or more electrical pulses can be generated using the septal annular pacing unit 310 of the pulse generator 100 for delivery to the heart. Thus, the pulse generator 100 can comprise a septal annular pacing unit 310 that includes circuitry for providing the electrical output stimulus. The septal annular pacing unit 310 is in electrical communication with the septal annular lead 319. Thus, the septal annular pacing unit 310 comprises circuitry configured to provide an electrical stimulus having predetermined electrical characteristics for selective delivery to the septal annular region.

The electrodes 320 can also be used to sense electrical activity in the tricuspid annular region and to deliver one or more electrical pulses to the tricuspid annular region. For example, the electrodes 320 can be positioned relative to the heart so that the electrical activity can be selectively detected in at the lateral annular region of the tricuspid annulus. Moreover, in the same position, the electrodes 320 can be used to deliver one or more electrical pulses selectively to the lateral annular region of the tricuspid annulus.

The sensed electrical activity can be communicated to the sensing unit 312 and the electrical pulses for delivery through the electrodes 320 can be generated using the lateral annular pacing unit 314 of the pulse generator 100. Thus, the pulse generator 100 can comprise a lateral annular pacing unit 314 that includes circuitry for providing the electrical output stimulus. The lateral annular pacing unit 314 is in electrical communication with the lateral annular lead 321. Thus, the lateral annular pacing unit 314 comprises circuitry configured to provide an electrical stimulus having predetermined electrical characteristics for selective delivery to the lateral annular region.

The control unit 322 receives signals from each sensing unit (306, 308 and 312) and generates trigger signals for each pacing unit (304, 310 and 314). The trigger signals cause the pulse generator 100 to deliver an electrical pulse through a given lead (315, 319 and 321) and electrode (316, 318 and 320) to the heart. The pacemaker 30 can further comprise memory 330 and a processor 328. The memory 330 and processor 328 can be coupled to the control unit 322 using the system bus 326. The memory 330 and processor 328 can function to direct the sensing and stimulation capabilities of the pacemaker through the control unit 322.

Optionally, the pacemaker 30 can further comprise a telemetry circuit 332 for communicating with processing systems remote to the pacemaker. The pacemaker 30 can also include a system control module 334 that can support circuitry for the processor 328, a telemetry interface 332, and a sleep-wake control.

Optionally, the pacemaker 30 can include a rate adaptive sensor 324 that is in communication with the control unit 322 through the system bus 326. The rate adaptive sensor 324 can be any sensor capable of sensing a physiological parameter related to the rate at which a heart should be beating. For example, the rate adaptive sensor can sense parameters such as oxygen content of blood, body motion, respiration rate and/or pH of blood. Parameters sensed by the rate adaptive sensor can be used to adjust aspects of the pacing timing and characteristics.

The pacemaker 30 can also comprise a battery 336, such as a lithium iodine battery, and a voltage supply 338 that can supply various current and voltage to the pulse generator 100. Optionally, the battery 336 can be integral with the pulse generator 100 or the supplied voltage can be communicated to the pulse generator 100. A given pacing unit (304, 310 and 314) can use the supplied voltage to produce an electrical stimulus for pacing the heart.

Although FIG. 3C illustrates aspects of an example cardiac pacemaker 30, similar electrodes, pulse generators, and sensing units can also be used with the example cardiac pacemakers 10 and 20. For example, the pacemaker 10 and pacemaker 20 can comprise bipolar leads with electrodes, associated sensing units, and pulse generators as described in reference to the pacemaker 30. Moreover, other example cardiac pacemakers, such as the pacemaker 10 and pacemaker 20 can comprise a control unit, a bus structure, a processor, memory, a telemetry unit, rate adaptive sensors, voltage supply and a battery as described for the pacemaker 30. Thus, for each lead, an example pacemaker (10, 20 or 30) can comprise a sensing unit and a pacing unit. In some optional examples, two or more leads can share a sensing unit and pulse generator, if for example, a lead adaptor 202 is used. Regardless of the number of leads, the pacemaker can comprise circuitry such as a control unit, processor and battery to provide sensing and/or pacing capabilities at one or more of the leads.

As shown in FIG. 3D, an example pacemaker device can also comprise a defibrillator lead 344. The defibrillator lead 344 can include an electrode that can be placed relative to the heart to provide a pulse of electricity to the tricuspid annular region. For example, the defibrillator lead 344 can be optionally positioned to selectively deliver a pulse of electricity to the septal annular region of the tricuspid annulus to provide defibrillation of the heart muscle. In another example, the defibrillator lead 344 can be optionally positioned to selectively deliver a pulse of electricity to the lateral annular region of the tricuspid annulus for defibrillation of the heart muscle. In either case, the defibrillator lead can be in communication with a defibrillator unit 342 which can be in communication with a high energy generator 340. A defibrillator unit 342 can be used in patients that are at risk of sudden cardiac death. A number of factors can contribute to the onset of a malignant heart rhythm (e.g. ventricular fibrillation or tachycardia) that can lead to sudden cardiac death. The ability to impart a sudden electrical energy using the defibrillator unit 342 can revert the heart back to a normal or less dangerous heart rhythm. The example device shown in FIGS. 1A and 1B can also be modified to include a defibrillator lead and a high energy generator. Thus, an example device can comprise a lead for selectively activating the tricuspid annulus region and a lead for defibrillation. An example method of pacing a heart comprises positioning an electrode relative to the heart so that an electrical stimulation pulse can be transmitted selectively to the tricuspid annular region of the heart. The method can further comprise transmitting an electrical stimulation pulse through the electrode selectively to the tricuspid annular region of the heart. The electrical stimulation pulse can cause electrical activity in the heart and can provide pacing of the heart.

Figure 5:
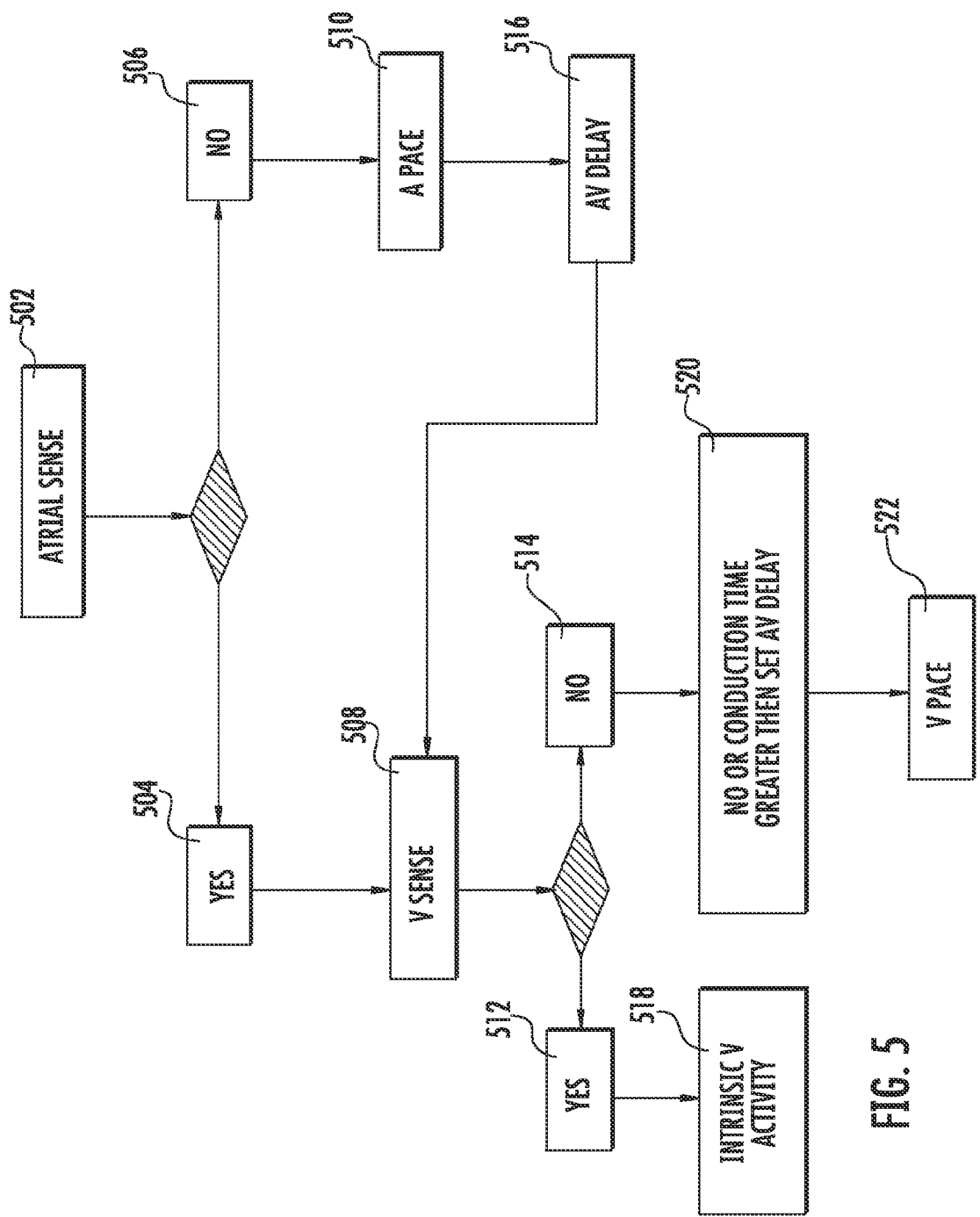
FIG. 5 is a flow diagram illustrating aspects of an example method of pacing a heart.

FIG. 5 is a flow diagram showing aspects of an example method of pacing a heart using a pacemaker having pacing electrodes positioned to selectively deliver an electrical pulse to the tricuspid annular region of a heart for pacing. At block 502, an atrial electrode is used to sense for electrical activity in the right atria of a heart. If atrial activity is sensed at block 502 (504), then a right ventricular electrode is used to sense electrical activity in the tricuspid annular region in block 508. If atrial electrical activity is not sensed at block 502 (506), then the atrium is paced at block 510 using the atrial lead, which delivers one or more electrical pulses to the right atrium tissue.

After pacing at block 510, a predetermined time for A/V delay is allowed to pass at block 516. After the A/V delay, the right ventricular electrode is used to sense for electrical activity in block 508. If no electrical activity is sensed at block 508 (514), or if the conduction time is greater than a set A/V delay (520), then an electrode positioned relative to the heart to deliver an electrical pulse selectively to the tricuspid annular region is triggered to pace the right ventricle 522. If electrical activity is sensed at block 508 (512), indicating intrinsic right ventricular activity 518, the ventricular lead can be refrained from delivering a pulse of electricity to pace the right ventricle.

Figure 6:
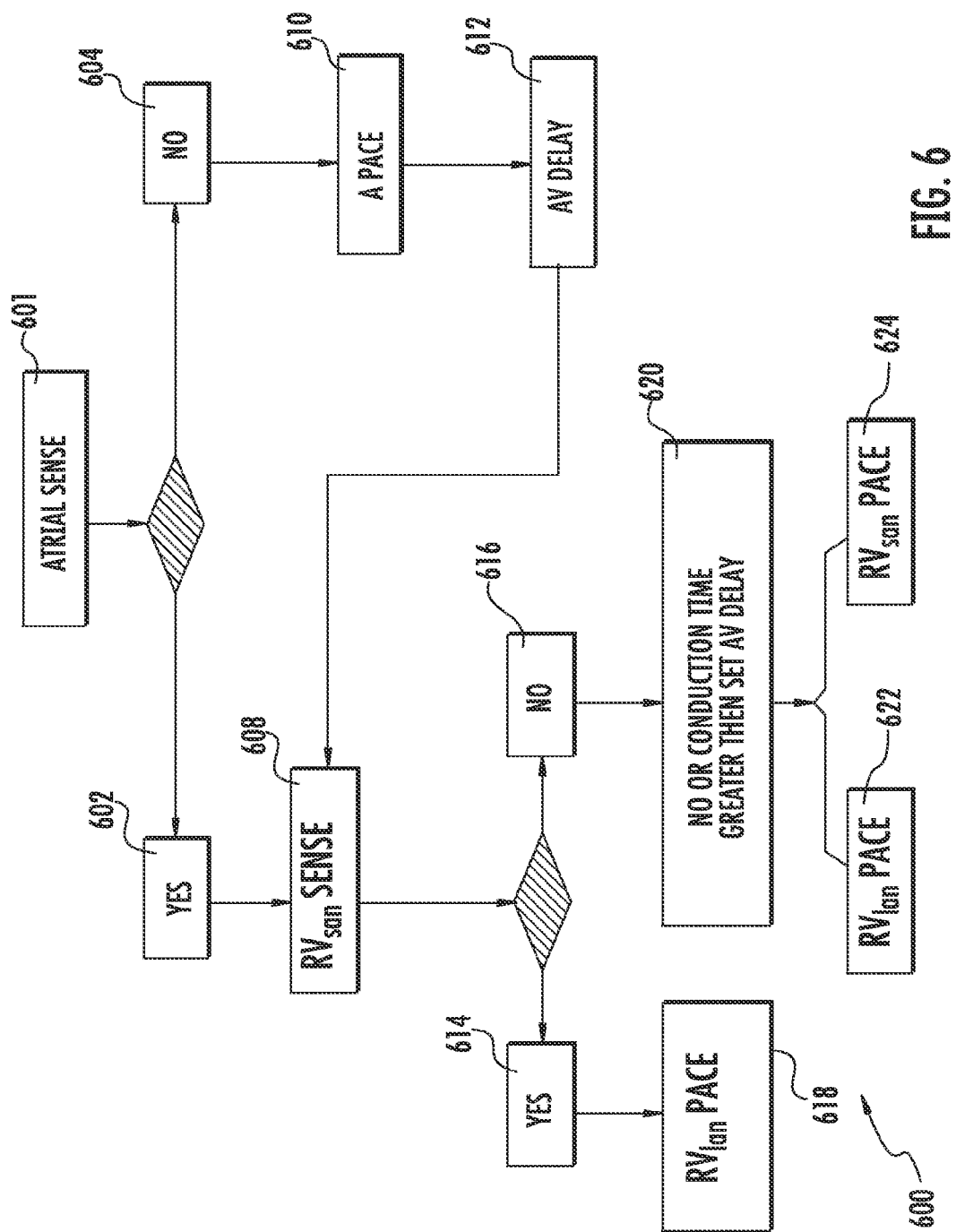
FIG. 6 is a flow diagram illustrating aspects of an example method of pacing a heart.

FIG. 6 is a flow diagram showing aspects of an example method of pacing a heart 600 using a pacemaker having two pacing electrodes positioned to selectively deliver one or more electrical pulses to the tricuspid annular region of a heart for pacing. In this example method, a first right ventricular electrode is positioned to selectively deliver one or more electrical pulses to the lateral annular region of the tricuspid annulus and a second right ventricular electrode is positioned to selectively deliver one or more electrical pulses to the septal annular region of the tricuspid annulus.

At block 601, an atrial lead is used to sense for electrical activity in the right atria of a heart. If atrial activity is sensed at block 601 (604), then a right ventricular lead positioned in the septal annular region of the tricuspid annulus is used to sense electrical activity in block 608. If atrial electrical activity is not sensed at block 601 (604), then the atrium is paced at block 610 using the atrial lead, which provides one or more electrical pulses to the right atrium tissue.

After pacing at block 610, a predetermined time for A/V delay is allowed to pass at block 612. After the A/V delay, the right ventricular lead positioned in the septal annular region of the tricuspid annulus is used to sense for electrical activity in block 608. If no electrical activity is sensed at block 608 (616), or if the conduction time is greater than a set A/V delay (620), then the electrode positioned relative to the heart to deliver an electrical pulse selectively to the lateral annular region of the tricuspid annulus (622) and the electrode positioned relative to the heart to deliver an electrical pulse selectively to the septal annular region of the tricuspid annulus (624) are triggered to pace the right ventricle.

Optionally, the septal annular lead electrode and the lateral annular lead electrode simultaneously stimulate the right ventricle to provide pacing. If electrical activity is sensed at block 608 (614), indicating right ventricular activity at the septal annular region of the tricuspid annulus, the RVlan lead can be used to deliver a electrical pulse to the lateral annular region of the tricuspid annulus 618.

Figure 7:
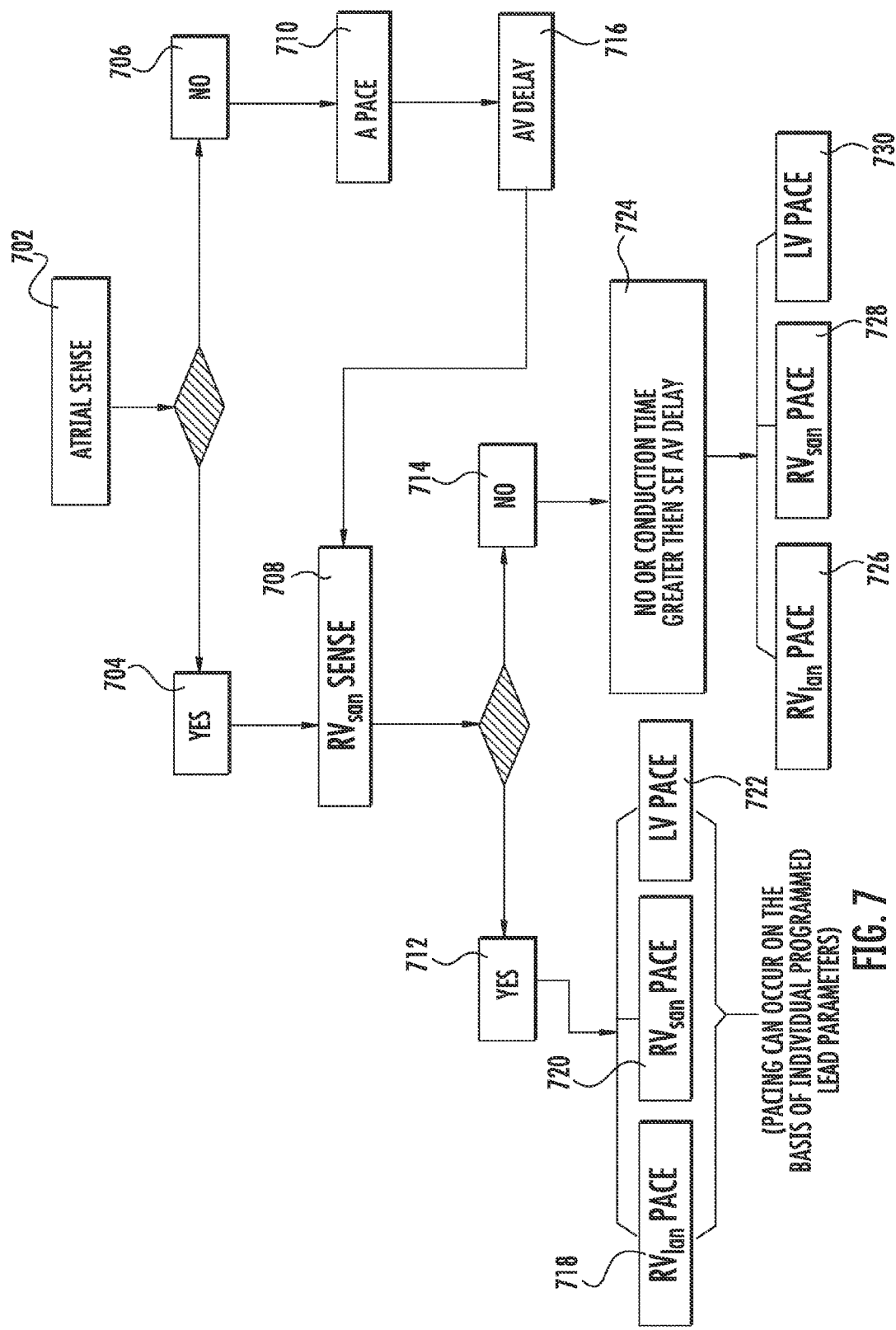
FIG. 7 is a flow diagram illustrating aspects of an example method of pacing a heart.

FIG. 7 is a flow diagram showing aspects of an example method of pacing a heart using a pacemaker having two pacing leads positioned to selectively deliver an electrical pulse to the tricuspid annular region of a heart for pacing. In this example method, a first right ventricular lead is positioned to selectively deliver one or more electrical pulses to lateral annular region of the tricuspid annulus and a second right ventricular lead is positioned to selectively deliver one or more electrical pulses to the septal annular region of the tricuspid annulus. This method also utilizes an atrial lead for sensing and/or pacing the right atrium and a lead for sensing and/or pacing the left ventricle.

At block 702, an atrial lead is used to sense electrical activity in the right atria of a heart. If atrial activity is sensed at block 702 (704), then a right ventricular lead positioned in the septal annular region of the tricuspid annulus is used to sense electrical activity in block 708. If atrial electrical activity is not sensed at block 702 (706), then the atrium is paced at block 710 using the atrial lead, which provides one or more electrical pulses to the right atrium tissue.

After pacing at block 710, a predetermined time for A/V delay is allowed to pass at block 716. After the A/V delay, the right ventricular lead positioned in the septal annular region of the tricuspid annulus is used to sense for electrical activity in block 708. If no electrical activity is sensed at block 708 (714), or if the conduction time is greater than a set A/V delay (724), then the electrode positioned relative to the heart to deliver an electrical pulse selectively to the lateral annular region of the tricuspid annulus (726) and the electrode positioned relative to the heart to deliver an electrical pulse selectively to the septal annular region of the tricuspid annulus (728) are triggered to pace the right ventricle. Optionally, the septal annular lead electrode and the lateral annular lead electrode simultaneously stimulate the right ventricle to provide pacing.

Moreover, as shown in block 730, the left ventricular lead can be used to pace the left ventricle in desired coordination with the pacing of the right ventricle. If electrical activity is sensed at block 708 (712) indicating right ventricular activity at the septal annular region of the tricuspid annulus, the RVlan, RVsan, and LV leads can all be used to deliver a electrical pulse to the heart tissue (718, 720, 722).

The described devices and methods can be used in number of clinical conditions including, for example, RV dysfunction/failure, severe tricuspid regurgitation (TR), pulmonary hypertension (PHTN), right bundle branch block (RBBB), congenital heart disease, congestive heart failure, heart failure due to LV dysfunction, in non-responders to conventional LV resynchronization therapy, atrioventricular conduction abnormalities, sick sinus syndrome, arrhythmia management, acute myocardial ischemia/infarction, acute pulmonary thromboembolism, and myocarditis.

To position an electrode to deliver an electrical stimulus selectively to the tricuspid annulus, anatomical features of the heart can be identified. Anatomical features can be visualized using imaging technologies such as fluoroscopy. For example, the lateral annular region and septal annular region of the tricuspid annulus can be identified during a procedure to place leads.

To identify the anatomical location of the tricuspid annulus and the location to place leads to transmit a stimulating pulse of electricity selectively to the tricuspid annulus, the RV inlet can be identified, which extends from tricuspid annulus to the papillary muscle insertion. The RV trabecular segment can also be identified, which extends from inferior to the RV inlet towards the RV apex and then towards the RV outflow. This portion is heavily trabeculated and is the usual site of pacemaker or ICD lead implantation in the RV. The RV outflow segment, also called infundibulum, can be identified as the smooth portion of the RV just below the pulmonary valve.

The crista supraventricularis is a muscular ridge that separates the tricuspid valve and the pulmonary valve. The crista cupraventricularis comprises the parietal band, septal band and the infundibular septum. The tricuspid valve comprises the tricuspid annulus, tricuspid leaflets and other associated structures including papillary muscles. Usually there are three tricuspid valve leaflets: Anterior, Medial/Septal and Posterior. The tricuspid annulus is a part of cardiac skeleton that anchors the tricuspid valve. The tricuspid annulus is made of the fibro-adipose tissue that electrically isolates right atria from right ventricle except in the region of the right fibrous trigone. The right fibrous trigone is an integral part of the cardiac skeleton that forms part of the tricuspid annulus. This portion joins together the aortic, mitral, and tricuspid valves. It is through the right fibrous trigone that the atrioventricular (His) bundle passes. Fluoroscopic views including right anterior oblique (RAO), left anterior oblique (LAO), anteroposterior and lateral views with varying angulations can be used to accurately define the cardiac landmarks including the tricuspid annulus, RV apex and RVOT. Echocardiography can also be used. Further, three dimensional cardiac mapping can be used with computed tomography or cardiac magnetic resonance imaging. Electrical mapping of the right ventricle can also be performed to determine electrical activation pattern and to determine areas that are activated last. Two example methods that can be used to fix the electrodes in the desired locations include use of a standard active-fixation pacing lead and use a catheter related to that used to map in a circle around the orifice of a pulmonary vein where it inserts into the left atrium. This catheter, frequently called a "halo" catheter, is straight when it is inserted into the heart, but the end can be caused to form a circle.

The tricuspid annular leads can be placed in the RV inflow to selectively transmit one or more pacing pulses to the tricuspid annulus. After identification of the anatomical areas of the tricuspid annulus using fluoroscopy, pacemaker leads are advanced into the right ventricle. Curved sheaths or stylets (e.g. a J-shaped stylet with secondary curvature) can be used to position the annular leads. Pacing from various regions of the tricuspid annulus can be performed to evaluate desired positions for the leads. The desired lead positions in the lateral and medial annular region can be defined by an intra-cardiac electrocardiogram where the A and V signal can be recorded. The annular lead position can be defined by a small A and a large V deflection on the intra-cardiac electrocardiogram. Moreover, as described above, pacing parameters can be evaluated using a PSA. Pacing parameters can include R>5 mV; threshold <2V at 1 msec. The lead position to selectively transmit one or more pacing pulses selectively to the tricuspid annulus can be further defined by a narrowing of the QRS complex or absence of widening of the QRS complex with pacing or the shortest paced QRS complex, improvement in tricuspid annular peak systolic excursion (TAPSE) and other echocardiographic features for improvement in right ventricular function, and/or improvement in cardiac output or RV stroke volume. Other echocardiographic and hemodynamic parameters can be used to indicate the desired position for the tricuspid annulus leads. These include absence of paradoxical motion of the intraventricular septum, preservation or improvement in LV ejection fraction and improvement in severity of tricuspid regurgitation. Electrocardiographic parameters that can also be used to position the tricuspid leads. These include concordance of QRS and T waves in precordial leads. Leads can be fixed by active fixation (e.g. screw) or passive fixation (e.g. tines).

Fluoroscopic views (RAO: right anterior oblique, LAO: left anterior oblique, AP: anteroposteior and lateral views with varying angulation) can be used to accurately define the cardiac landmarks including tricuspid annulus, RV apex, and right ventricular outflow tract (RVOT).

After the location for lead placement is identified anatomically, the location can be adjusted based on electrophysiological evaluation including hemodynamic improvements demonstrated in an electrophysiology lab. Echocardiography can be also be used to determine the location for placement of the RV electrodes. Baseline evaluation of LV and RV function can also be performed. For example, measurement of tricuspid annular peak systolic excursion (TAPSE) can be performed. Hemodynamic measurements including cardiac output and stroke volume can also be determined.

Prior to implantation of the pacing leads, an electrophysiological study of the heart can be performed. The electrophysiological study can help map the tricuspid annulus area accurately. His and Para-Hisian areas can also be mapped. After identification of the various areas of tricuspid annulus, one or more leads can be advanced into the right ventricle.

The devices can be placed in a subject in an electrophysiology lab or in a clinical operating environment. Thus, the devices can be placed in a properly equipped surgical suite or cardiac catheterization laboratory. Two example routes of pacemaker lead implantation include an endocardial route and an epicardial route.

Using an endocardial approach, a RVsan unipolar/bipolar lead can be placed in the proximal interventricular septum. The lead can be fixed using active or passive methods. Also, using an endocardial approach, a RVlan unipolar/bipolar lead can also be placed in the lateral wall of right ventricle to selectively deliver one or more pacing pulses to the tricuspid annulus. The lead can be fixed by active or passive methods. Other leads can be placed in the atria and LV at conventional locations and using conventional endocardial techniques based on the clinical indication.

Using an endocardial lead implantation approach, surface ECG leads can be placed on the subject for obtaining surface electrocardiogram. Routine cardiac/hemodynamic monitors can be applied to the subject for non-invasive monitoring. The area for arterial and venous access is cleaned with anti-septic solutions. Strict aseptic precautions can be taken throughout the procedure. Lidocaine solution can be used for local anesthesia. Anxiolytics and sedatives such as midazolam can also be used. Empiric antibiotics can be used prophylactically. Oxygen saturation can be monitored continuously and oxygen can be supplied by a face mask if the saturation drops below 90%.

A single incision of approximately 3-5 cm can be made at the left deltopectoral groove and a subcutaneous pocket is manually formed for placement of the device. With use of the same incision, a small pocket can be formed at the upper site for final lead placement to avoid contact with the device. Venous access through cephalic or subclavian vein can be used for lead access. In specific instances, other venous approaches can also be used such as saphenous and external jugular vein.

A J-guide wire can be used to guide the passage of an introducer sheath. After removal of the guide and dilator, the endocardial leads can be advanced under fluoroscopic guidance into the right ventricle. Endocardial electrograms can be recorded and analyzed for amplitude and the presence of an injury current. Sensing and pacing characteristics can be then assessed, as well as, impedance and slew rate. In some instances, the lateral annular lead can be placed via the right ventricular marginal vein. Once the leads are in proper place, the subject can be asked to take deep breaths and cough vigorously while the leads are observed under a fluoroscope. This is done to ensure proper and secure placement of the leads. The leads can be then attached to device. The lead system is actively fixated at the muscular fascia with mersilene (Ethibond®, Ethicon, Inc., Somerville, N.J.) sutures and subcutaneous tissue closed with Vicryl® (Ethicon, Inc., Somerville, N.J.) sutures. The skin is closed intracutaneously with self-dissolving Vicryl® (Ethicon, Inc., Somerville, N.J.) sutures.

Using the epicardial approach a RVsan unipolar/bipolar lead can be placed near the proximal interventricular septum. The lead can be fixed using an active or passive method. Also using the epicardial approach a RVlan unipolar/bipolar lead can be placed in the lateral wall of right ventricle epicardially near the tricuspid annulus. The lead can be fixed using active or passive methods. Other leads corresponding to the atria and LV can also be placed using the epicardial approach, which can be placed conventionally based on the clinical indication. A combination of endovascular and epicardial approaches can also be used for the implantation of the leads. Once implanted, a standard pacing system analyzer can be used to test the pacing threshold (volts), lead impedance and R wave amplitudes.

Using epicardial lead implantation an incision is made in the chest to expose the exterior surface of the heart. The lead is attached directly to the designated points on the heart's surface (epicardium). This method of placement can be performed under general anesthesia. Minimally invasive procedure/thoracoscopic procedures can also be used for such a lead implantation. The pulse generator can be placed under the skin in the upper abdomen, but it can also be placed in the upper chest area. This lead placement method can be used when there is a clinical indication to avoid the endocardial positioning method.

Pacing from various regions of tricuspid annulus can be used to evaluate the position of annular leads. Lead positioning in the lateral and septal annular region can be determined by identifying a narrowing of the QRS complex, an absence of widening of QRS complex with pacing, or the shortest paced QRS complex. Lead positioning can also be determined by an improvement in TAPSE (tricuspid annular peak systolic excursion) measured by echocardiography as compared to baseline. Lead positioning can also be determined by an improvement in cardiac output or RV stroke volume. Other associated echocardiographic and hemodynamic parameters can also be used to indicate the pacing site for selectively delivering electrical stimulation to the tricuspid annulus. These include absence of paradoxical motion of interventricular septum, preservation or improvement in LV ejection fraction and improvement in the severity of tricuspid regurgitation. Other associated electrocardiographic parameters that can indicate the lead positioning to selectively stimulate the tricuspid annulus include concordance of QRS and T waves in precordial leads. The leads can be fixed in a location for selective delivery of electrical stimulation to the tricuspid annulus by active fixation (e.g. a screw) or by passive fixation (e.g. tines). After lead placement, pacing thresholds and impedances can be measured to evaluate the integrity of lead implantation.

A number of embodiments have been described. Nevertheless, it will be understood that various modifications may be made without departing from the spirit and scope of the invention. Accordingly, other embodiments are within the scope of the following claims.

What is claimed is:

1. A method for pacing a heart, comprising:
   (a) positioning a first electrode relative to the heart, wherein an electrical stimulation pulse can be transmitted selectively to the septal annular region of the tricuspid annulus of the heart;
   (b) positioning a second electrode so that an electrical stimulation pulse can be transmitted selectively to the lateral annular region of the tricuspid annulus of the heart; and
   (c) transmitting an electrical stimulation pulse from the first electrode selectively to the tricuspid annulus of the heart, wherein the electrical stimulation pulse causes electrical activity in the heart to provide pacing; and
   (d) transmitting an electrical stimulation pulse through the second electrode selectively to the lateral annular region of the heart, wherein the electrical stimulation pulse causes electrical activity in the heart to provide pacing.

2. The method of claim 1, wherein an electrical stimulation pulse is transmitted through the first electrode and an electrical stimulation pulse is transmitted through the second electrode at substantially the same time to provide pacing.

3. The method of claim 1, further comprising sensing electrical activity from the tricuspid annular region.

4. The method of claim 3, wherein an absence of sensed electrical activity triggers the transmission of an electrical pulse to the tricuspid annular region.

5. The method of claim 3, wherein a conduction time greater than a set atrial-ventricular delay time triggers the transmission of an electrical pulse to the tricuspid annular region.

\* \* \* \* \*